United States Patent [19]

Chang et al.

[11] Patent Number: 4,915,237

[45] Date of Patent: * Apr. 10, 1990

[54] COMPREHENSIVE CONTAINER INSPECTION SYSTEM

[75] Inventors: Roger Chang, Ft. Lauderdale; Donald Darling, Palm Beach Gardens; Jaime Periera, North Palm Beach; Mark Filipowski, Lake Worth; Tyce Fitzmorris, Lake Park; Trent Francis, Ft. Lauderdale; Dale Kline, Palm Beach; Russell Mortenson, West Palm Beach; Steven R. Rowley, West Palm Beach; Timothy Wagner, West Palm Beach, all of Fla.

[73] Assignee: Inex/Vistech Technologies, Inc., Clearwater, Fla.

[*] Notice: The portion of the term of this patent subsequent to Jun. 7, 2005 has been disclaimed.

[21] Appl. No.: 906,299

[22] Filed: Sep. 11, 1986

[51] Int. Cl.⁴ ............................................... B07C 5/00
[52] U.S. Cl. .................................... 209/524; 198/372; 198/406; 198/410; 209/526; 209/538; 209/548; 209/652; 209/939; 356/428; 358/106
[58] Field of Search ................ 358/106.107, 101; 250/223 B, 224; 356/428, 240, 23; 209/526, 523, 707, 539, 524, 701, 538, 656, 651–654, 939, 936, 548, 542; 198/370, 372, 406, 409, 410

[56] References Cited

U.S. PATENT DOCUMENTS

| | | | |
|---|---|---|---|
| 1,476,023 | 12/1923 | Phelps | 198/358 |
| 2,085,410 | 6/1937 | Bergman | 198/441 |
| 2,368,350 | 1/1945 | Ellison | 356/428 |
| 2,393,188 | 1/1946 | Reynolds | 209/524 |
| 2,461,290 | 2/1949 | Maynard et al. | 128/406 |
| 2,529,081 | 11/1950 | Hughes et al. | 209/652 |
| 3,160,277 | 12/1964 | Wyman | 209/523 |
| 3,421,616 | 1/1969 | Jenner | 209/523 |
| 3,901,381 | 8/1975 | Quinn | 198/283 |
| 3,920,541 | 11/1975 | Vanden Berg et al. | 209/587 |
| 3,941,686 | 3/1976 | Wyman | 209/523 |
| 4,136,930 | 1/1979 | Gomm et al. | 358/106 |
| 4,207,974 | 6/1980 | Dragotta | 198/344 |
| 4,295,558 | 10/1981 | Heckman | 198/440 |
| 4,376,951 | 3/1983 | Miyazawa | 356/240 |
| 4,378,494 | 3/1983 | Miller | 356/240 |
| 4,380,025 | 4/1983 | Deane | 358/106 |
| 4,380,026 | 4/1983 | Kubota | 358/106 |
| 4,446,481 | 5/1984 | Edamatsu et al. | 358/106 |
| 4,479,582 | 10/1984 | Ducloux | 209/552 |
| 4,486,776 | 12/1984 | Yoshida | 358/106 |
| 4,582,201 | 4/1986 | Taniguchi | 209/587 |
| 4,670,788 | 6/1987 | Ozaki | 358/106 |
| 4,679,075 | 7/1987 | Williams et al. | 358/106 |
| 4,680,463 | 7/1987 | Lutgendorf et al. | 356/240 |
| 4,691,231 | 9/1987 | Fitzmorris et al. | 209/526 |
| 4,750,035 | 6/1988 | Chang et al. | 358/106 |

Primary Examiner—Donald Hajec

[57] ABSTRACT

A comprehensive container inspection system includes axial container examining features, side wall inspection features and a controllable diverter for routing the containers to one of at least two sorting paths. Each stage of the inspection system is adapted to process moving containers, a continuous line of moving containers being processed and controllably diverted without stoppages. In an axial inspection area, containers are carried through rim, energy absorption and base inspection areas by means of side rollers bridging a gap in endless belt conveyor sections. In a side wall inspection area, containers are continuously rolled before a video detector operable to record and analyze images including at least three of the rolling bottles. A downstream mechanical diverter device includes a picker element operable to stop a container ahead of a container to be diverted, and means for positioning the diverted container to be squeezed into a diversion path between the stopped container and a next container, the next container advancing continuously through the diversion process.

16 Claims, 5 Drawing Sheets

COMPREHENSIVE CONTAINER INSPECTION SYSTEM

BACKGROUND OF THE INVENTION

1. Field of the Invention

This invention relates to the field of article inspection, and in particular to an inspection system for transparent and translucent containers such as bottles. Means are provided to comprehensively examine each successive bottle in a line of adjacent bottles along a moving conveyor, without stopping them, including examination of container rims, bases, energy absorption and sidewall characteristics, using video detectors and energy absorption comparison means.

2. Prior Art

Various inspection systems have been attempted in which a plurality of containers such as glass bottles moving along a conveyor are automatically examined and automatically sorted based upon characteristics discovered. Although certain steps and certain elements of inspection apparatus have become quite sophisticated, it is not readily possible to arrange an inspection system in a comprehensive manner such that inspection can proceed smoothly and continuously without deliberately or inadvertently stopping the line and interfering with production processes upstream. Many disclosures of devices of this type employ apparatus that are regularly disruptive of smooth flow. Examples of such disruptions may be, for example, devices that remove containers from a straight conveying path for inspection, kickers, rotators, separators and diversion elements that are prone to knock containers down, and inspection stations that require some or all of the containers to be stopped in place, for example to be rotated and/or examined from a plurality of unobstructed angles that require a large conveyor section.

Reference may be made to various disclosures of particular arrangements by which rim inspection, base inspection, absorption or side wall inspection are carried out. Pat. 4,454,542-Miyazawa discloses a video rim inspection technique. Patents 4,391,373-Wiggins and 4,213,042-Beach, et al, disclose rim inspection devices including photocell pairs. Patents 3,932,042-Faani, et al, Re28,984-Drinkuth, et al teach side wall inspection techniques. Pat. 4,121,103 and 3,225,191, both to Calhoun, teach absorption and base analysis devices. These patents illustrate high levels of sophistication in the individual inspection procedures, criteria and means for discriminating and sorting containers. They do not, however, provide a system by which a plurality of such high quality individual inspection techniques can be coordinated, simultaneously or sequentially carried out, and resulting sorting of containers accomplished without either the regular stoppage of conveyors, or requirements due to timing, bottle separation rquirements or the like that interfere with flow of a continuous line of immediately-adjacent containers in a production plant or the like.

According to the invention, the containers are processed in a continuous line, each container resting directly against or positioned very close to adjacent containers, and the entire line moving continuously at high speeds. The containers need not be spaced for inspection, means being provided to conduct the necessary steps while the containers remain adjacent and moving.

According to the invention, means are provided bridging a gap defined between endless belt conveyor sections supporting containers from underneath, the bridge section having container side support belts frictionally engaging container sidewalls, for carrying the containers through inspection steps requiring axial viewing and/or exposure of the containers. The containers remain in a continuously-moving line. In the side wall inspection area, a video inspection system characterized by precise synchronism between bottle position and data capture additionally includes a bottle turning mechanism at the inspection zone by which all the containers passing without interruption one against another through the side wall inspection zone are turned continuously as they move along this part of the conveyor. A stationary rail on one side is opposed by a driven belt on the other side, for example moving at twice the conveyor speed, thereby rolling the bottles at full speed as they move continuously without generation of gaps.

The image recorded during sidewall inspection preferably encompasses several bottles. The video inspection means can be operable to analyze and reject for any defect found, and preferably also associates together the areas of successive several-bottle images that refer to a given container as it advances through the inspection zone, being rolled along the rail.

A downstream diversion element uses the moving bottles to squeeze out containers to be diverted from the line, allowing containers arriving in a continuous line to be smoothly sorted. This is accomplished by at least one and preferably two container support star wheels and a movable obstruction that, together with means for stopping a non-diverted bottle, squeeze the diverted bottle into a side path along a tangent to the at least one star wheel.

The invention as so described is a comprehensive bottle inspection system that is capable of all the sophistication of image analysis possible, yet does not interfere with container production and processing, the containers remaining adjacent one another in a continuously moving line.

SUMMARY OF THE INVENTION

It is an object of the invention to provide a comprehensive container inspection system especially for glass and plastic bottles, in which the inspection system does not impede or obstruct flow of containers.

It is another object of the invention to smoothly coordinate axial inspection steps and side wall inspection steps in a comprehensive system including a diversion mechanism for separating containers according to detected attributes.

It is another object of the invention to improve axial inspection, side wall inspection and container diversion techniques in ways that adapt certain known techniques for processing on a continuous line of moving bottles.

It is still another object of the invention to serve the foregoing objects in a device having a maximum of dependability and accuracy, and a minimum of expense.

These and other objects are accomplished by a comprehensive container inspection system that includes axial container examination features, side wall inspection features and means for controllably diverting the containers along one of at least two sorting paths. Each stage of the inspection system is adapted to process moving containers, a continuous line of moving containers being processed and controllably diverted without stoppages. In an axial inspection area, containers are carried through video rim inspection, energy absorption and base inspection areas by means of side rollers carrying the containers across a gap between endless belt conveyor sections. In a side wall inspection area, containers are continously rolled before a video detector operable to record and analyze images including three of the rolling bottles. Preferably, analysis includes associating those portions of successive images for data attributable to a given bottle as it advances through the multiple-bottle inspection zone. A downstream mechanical diverter device includes a picker element operable to stop one container ahead of a container to be diverted, and means for positioning the diverted container in position to be squeezed between the stopped container and a next moving container to thereby force the diverted container into a diversion path, the next container advancing continuously during the diversion process.

BRIEF DESCRIPTION OF THE DRAWINGS

There are shown in the drawings the embodiments that are presently preferred. It should be understood, however, that the invention is not limited to the precise arrangements and instrumentalities shown in the drawings, wherein.

DETAILED DESCRIPTION OF THE PREFERRED EMBODIMENTS

The system is described herein with reference to bottles, soft drink bottles and like containers. It should be noted that although glass bottles may be the preferred subject of inspection the invention is also applicable to other subjects, including other shapes, other materials and other opacities.

Figure 1:
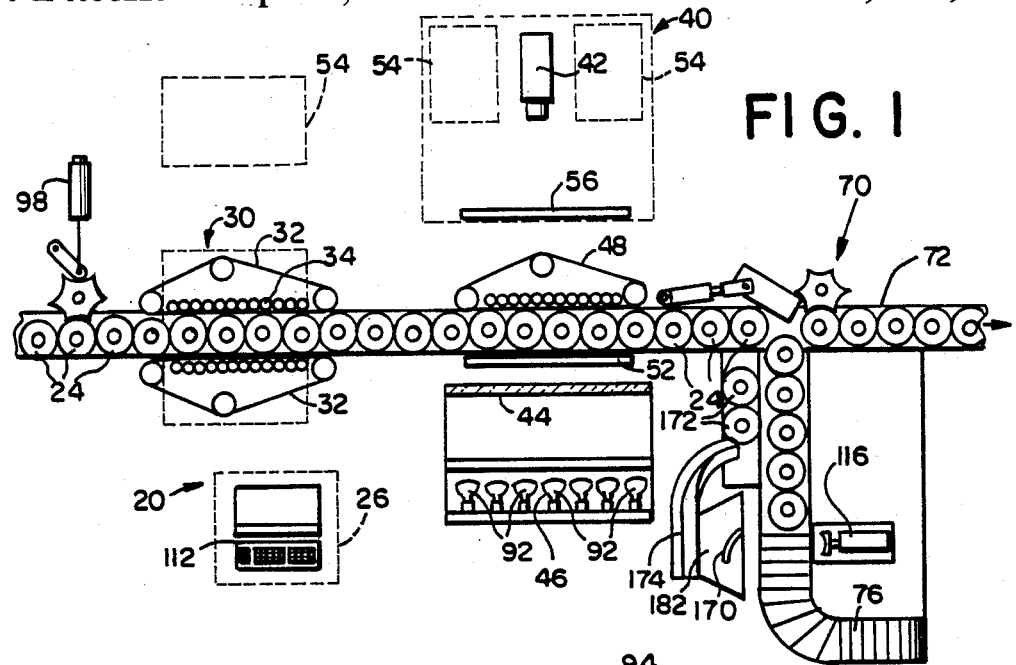
FIG. 1 is a plan view of a comprehensive inspection system according to the invention.
Figure 6:
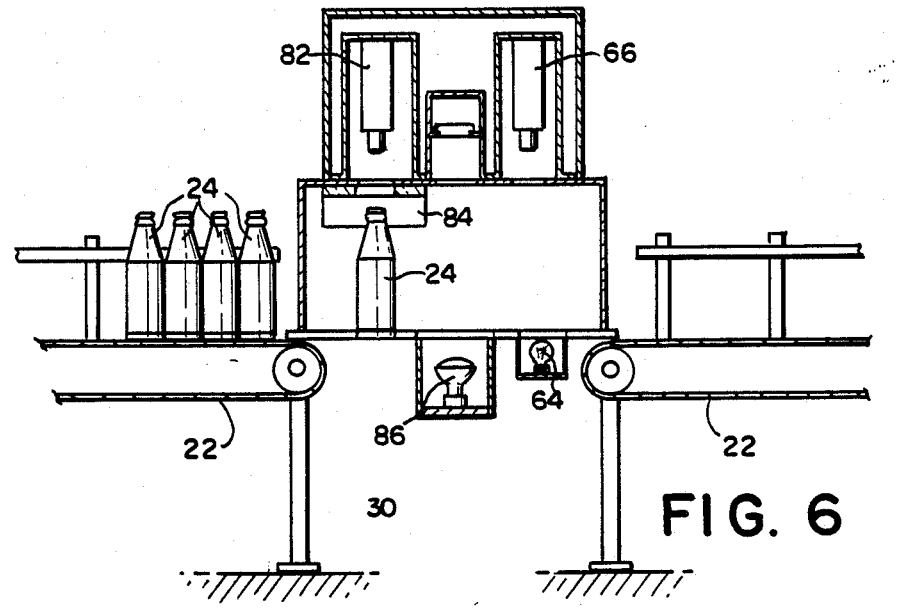
FIG. 6 is a partially cut away elevation view of the axial inspection station of the invention.
Figure 7:
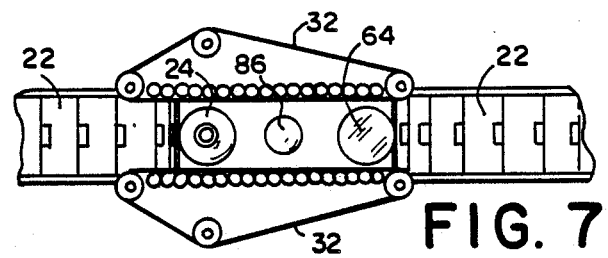
FIG. 7 is a top plan view taken along lines 7—7 in FIG. 6.

FIG. 1 is a plan view showing the comprehensive system of the invention. Generally, an axial inspection section 30 having a plurality of separate container exposure/viewing stations is located at a bridge between conveyor sections 22. Sections 22, as shown in FIG. 6, have a belt disposed under the containers, but side belts 32 carry the containers across a gap between sections 22 where unobstructed axial viewing of the containers is obtained. Results of the axial inspections for each container are preferably stored in control electronics 54, which includes a data processor operable together with a container counter 98 to keep track of the status of containers 24 advancing along the conveyor continuously. It is also possible to mark containers exiting the axial inspection with a dye or other marking that will be detected downstream. For example, a dye mark can be detected by the sidewall inspection system as a defect, for example due to opacity, lines of contrast, etc. Alternatively, a separate dye mark detector can be used at a point well downstream and clear of the inspection system, where it may be more convenient to carry out rejection and/or selection of containers. This allows versatility in line layout and avoids exposing containers to the dust and dirt of disposal functions.

A user-operated control station 26, including a display apparatus 112, is attached to the system for manually monitoring operation, for viewing samples of individual tests, and for displaying reports, alarms and the like. Containers advancing along the conveyor through counter 98 are inspected at side wall inspection area 40, at which an elevation view of a plurality (e.g., three) containers is captured and analyzed as each container passes a predetermined location, for example triggering capture of an image frame by breaking a photocell beam. The containers are rolled by one or more side-applied belts as they advance continuously through side wall inspection area 40. The side wall inspection apparatus is also monitored and controlled by control and power supply electronics 54 at one or more of the locations shown, including a digital computer operable to process and analyze data to determine the presence of certain defects in views and possibly to correlate the views. Of course, should a given container be flagged after failing upstream axial inspection, then the processor need not undertake side wall inspection, except if desired to develop statistical data of the occurrences of certain defects. That container can simply be rejected.

The system as shown preferably includes a container turner having a stationary side rail 52 opposed by a belt 48 driven at twice the conveyor speed. This is quite stable, allowing the containers to be turned nearly a full revolution within the space of the containers, with one recorded frame including three containers in progress. It is also possible to employ a second moving belt in place of side rail 52. The velocities of the opposed moving belts can be selected to turn the containers as needed to accommodate the detail of inspection and throughput needed. For example, by moving belt 48 less than twice the conveyor speed, a container will turn less than 120 degrees in the linear space of a bottle diameter. Should opposed belts be arranged to turn containers 60 degrees within the same linear space, then the inspection system can be made to record six containers per frame, etc. This allows a frontal view of each container from six angularly-spaced views.

Minimizing the extent of rotational energy transmitted to the container is a means of improving container stability. Therefore, reducing the rotation angle between containers can facilitate increasing the linear speed of the conveyor. In the example, using opposed belts to rotate one sixth of a revolution per linear diameter rather than a third, permits increasing the line speed from 600 to 1200 containers per minute, without loss of stability causing undue wear and breakage. At the same time the views spaced by 60 degrees are fully redundant front views of or through the whole surface area of the containers.

Also under control of processor is a downstream mechanical sorting station 70 that is adapted to sort containers advancing continuously at full speed, each container being immediately adjacent and possibly touching the two adjacent containers on either side.

The inspection system can be placed downstream of a container production or washing facility, and used to sort good containers from those that require reprocessing or rejection. Inspection can discern between types of bottles, rejectable bottles for certain types of defects only, and for certain attributes of goods bottles, for example wear characteristics. Bottles 24 arrive at the station on the left and after inspection depart along good bottle route 72, or are diverted to be rejected by ram 116 bumping the containers into reject hopper 74, or advance along route 76 for further examination or reprocessing. Route 76 can terminate in a table area where containers accumulate for manual inspection and appropriate sorting.

Figure 2:
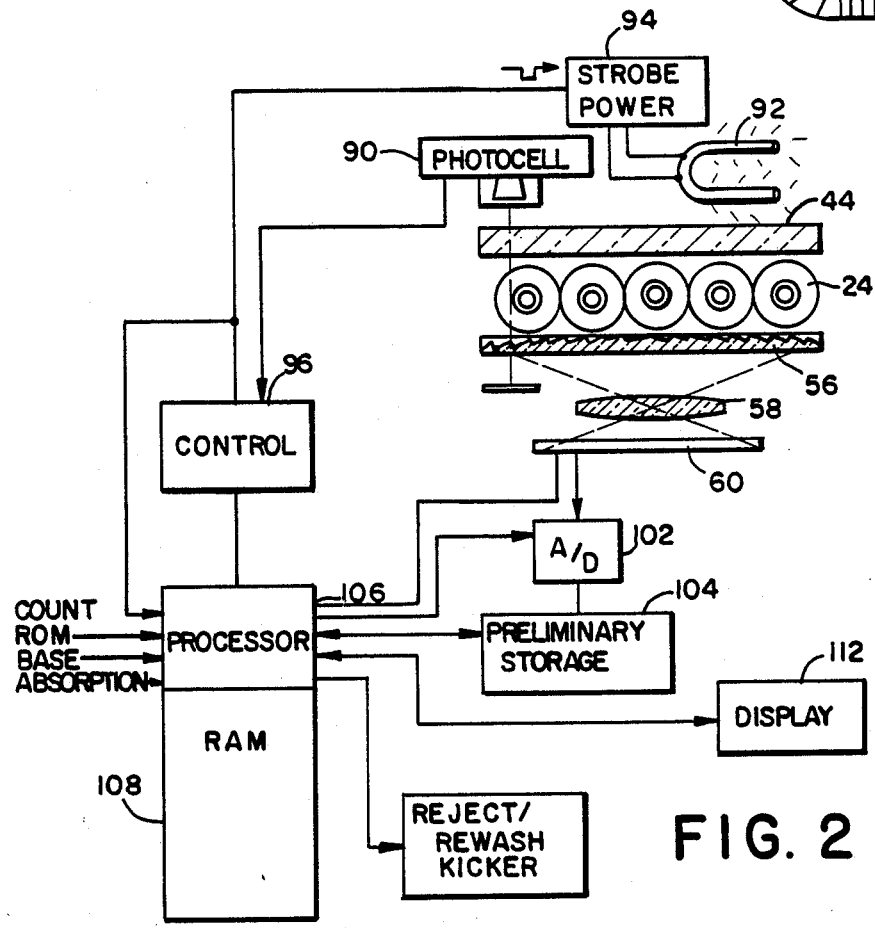
FIG. 2 is a schematic block diagram illustrating the processor of the invention, located in the side wall inspection section, and showing its interconnection to the axial inspection section and to the container sorting mechanism.

FIG. 2 shows a schematic layout of the side wall inspection system and the interconnection of the axial inspection elements with the digital computer processor. The processor may be located in the housing enclosing the side wall inspection area, or at one of the available enclosures 54. The processor can also be located, for example, in the console area 26, in the axial inspection area 30 or in other convenient places.

Whenever a continuously moving bottle 24 breaks the beam of bottle position photocell 90, a triggering signal is generated. The triggering signal triggers strobe power supply 94 and operates strobe lamp 92 to momentarily illuminate bottles 24, "freezing" them in place. Light emitted from strobe lamp 92 is diffused through translucent panel 44, and focused by means of collimator 56 and video camera optics 58 onto a planar optical detector 60, for example a charge coupled video detector device (CCD) having 480×365 pixels, and producing addressable analog levels as a function of the light received at the individual pixels from the containers.

The operation of strobe 92 and the resulting exposure of planar detector element 60 to the light emitted from strobe lamp 92 and the container being inspected, is preferably synchronous insofar as possible with the triggering signal of photocell 90. The strobe is controlled by means 96, responsive to photocell 90 and to processor 106 such that there is a possible short delay in triggering due to synch timing of processor 106. Insofar as possible, synchronous operation is achieved by replacing the standard free running synchronization of a CCD video camera with a one shot-type control 96 such that the device stores a single frame responsive to triggering from photocell 90 and not to a free running oscillator that merely accepts the next available frame as the image. Immediately after capturing the data by light activation of pixels on CCD 60, control means 96 triggers processor 106 to sequentially address the individual pixels of CCD 60, the output of which is converted to an RS-170 video signal. A/D converter 102 then samples the video signal and converts the respective analog levels to digital bytes in an array of 256×256 pixels. More pixels (and better resolution) may be appropriate, but increase processing time. The whole one shot of image data is stored in a preliminary storage 104, which may be a part of the processor RAM 108, and which data is then analyzed and, preferably, associated with other data for the same container (a).

The image is characterized by very-repeatable bottle position due to its capture synchronously or nearly synchronously with operation of photocell 90. The further display and analysis on the captured data can be conducted without particular synchronization being crucial. By capturing the signal entirely synchronously with operation of photocell 90, a freeze frame is achieved in which the image of the successive bottles is located at precisely the same relative location in the video image. Such operation can be distinguished from general video inspection techniques in which an article position signal gates through the next frame-grabbing operation. In a conventional system, a free running video data collection device having an internal free-running frame synch is simply triggered to treat the next full frame as the captured video image data. Typically, video systems are operated such that 30 frames are captured per second, and in a continuously-moving conveyor stream, an uncertainty of positioning of a full thirtieth of a second can cause substantial jitter in the position of the containers in the image. The invention avoids such jitter and as a result avoids the necessity of searching a substantial area of each frame during data analysis to locate a leading edge of a container. Moreover, the frame is more efficiently allotted to exposure of a plurality of containers, rather than to extra space needed to accommodate possible jitter effects.

It is also possible to use additional processors, perhaps sharing memory elements, to accomplish functions of control and analysis. Photocell 90's triggering signal can be connected as an interrupt to video processor 106, with an interrupt service subroutine handling addressing and/or shifting control of data read out from CCD 60 for generating a video signal, converting the signal to digital format and storage. The possibility of some minor jitter occurs because processor 106 can be processing a higher priority interrupt or otherwise occupied in capturing volatile data.

Figure 3:
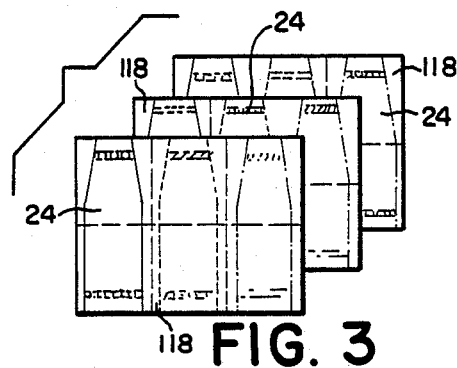
FIG. 3 is a schematic representation of a plurality of successive side wall data images, showing the advance of a predetermined bottle along the conveying path in successive images.

One or more processors 106, which can also be connected to the axial inspection apparatus, and to means such as photocell 90 for counting containers. Processor 106 includes a section of random access memory 108, which may be internal RAM including not only programming and intermediate data analysis information, but also including an image buffer adapted for storing successive images captured for preliminary storage, and including buffer 104, upon the passage of successive bottles through a predetermined location at which they break the beam of photocell 90. As shown in FIG. 3, a given bottle 24 advancing from left to right appears successively at the left, middle and right positions in successive frames 118, respectively. Processor 106 will cause rejection of containers showing defects in any of the views and furthermore is preferably adapted to associate these successive frames as being views of a single bottle 24. Accordingly, wear, existence of labels, etc. can be correlated from view to view. At the end of the three frames, the axial inspection and side wall inspection data can be analyzed and further correlated. The particular analyses undertaken are not treated extensively in this application. Nevertheless, it will be appreciated that pixel data from the respective images can be used to sort containers based upon dirt, defects, wear, container type, brand type or other attributes.

Figure 4:
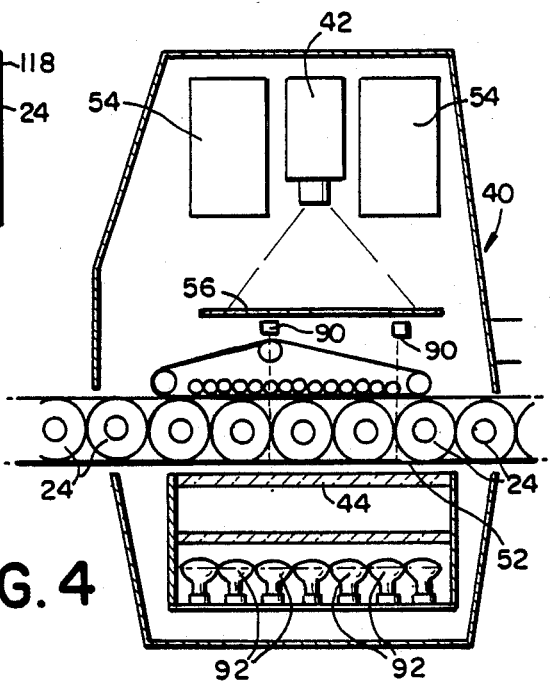
FIG. 4 is a partial section of the side wall inspection unit, in plan.
Figure 5:
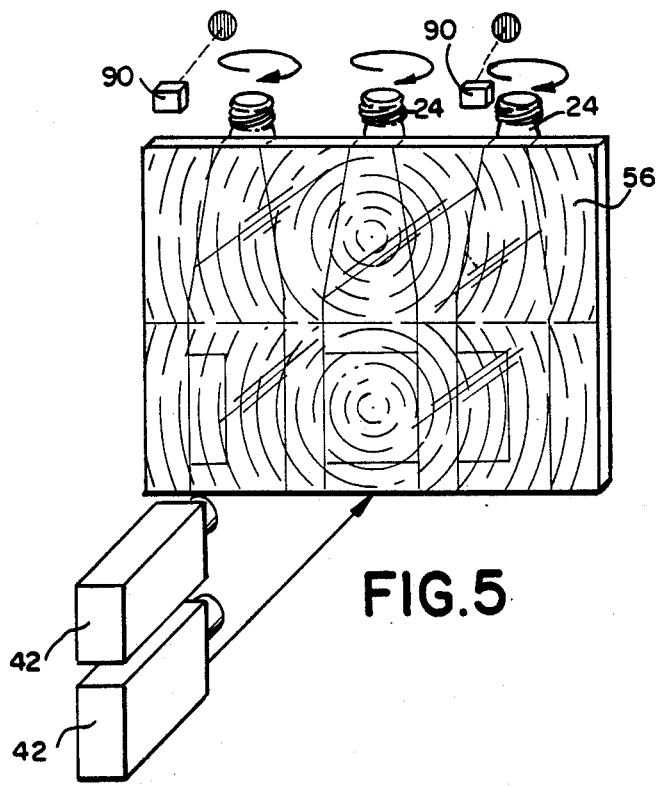
FIG. 5 is a perspective view illustrating advance of the containers in the side wall inspection section.

FIG. 4 is a more detailed view of side wall inspection unit 40. As containers pass along the conveying path moving from left to right, containers breaking the beams of photocells 90 trigger a flash from strobe lamps 92, located behind one or more diffuse panels 44, tending to produce an evenly back lighted view of three containers 24. Strobe lamps 92 are evenly distributed along the conveying path and also are evenly distributed in elevation within the back lighting enclosure.

In order to develop angularly spaced views of the containers 24, the containers are rotated in the side wall inspection area. A stationary rub rail 52 or slow moving belt, for example of wear resistant rubber, is mounted along one side of the conveyor. On the opposite side of the conveyor, a faster driven belt 48 is urged against the containers 24 by a series of supporting rollers. Belt 48 is driven at a greater speed than the conveyor, whereby the bottles rotate when moving through the inspection area. It is preferred for a three-container frame view that driven belt 48 be opposed by the stationary rail and moved at precisely twice the speed of the conveyor, preferably coupled by mechanically gearing the drive of belt 48 to the conveyor drive. Inasmuch as belt 48 moves at twice the conveyor speed while the opposite wall is stationary, the containers continue to move along the conveyor at the average of the opposed wall speeds, i.e., at the conveyor speed. Belt 48 is preferably tensioned by a pneumatic cylinder (not shown) or the like urging its idler pulleys outwardly.

Preferably, two cameras 42 are stacked over one another, one viewing the upper halves of the containers and the other viewing the lower halves. Inasmuch as cameras 42 record images of three containers simultaneously, there would normally be substantial perspective effects of viewing, interfering with the full availability of data. Accordingly, a collimator 56 is placed between containers 24 and video cameras 42, to thereby provide a true elevation view of the containers. Collimator 56 is preferably a segmented fresnel les having upper and lower parts aligned to viewing axes of cameras 42. The elevation view limits the effective coverage of the container label to the label's true height, and avoids a situation in which the label or its shadow obstructs a larger portion of the back side wall than the front side wall due to divergence of perspective viewing lines from the video detector.

FIG. 6 illustrates greater detail of the axial inspection section 30. Conveyor segments 22, which are endless belt drives, carry containers 24 from underneath, but define a gap in the area of axial inspection station 30. In this station, the containers are carried by two opposed belts 32, applied to the sides and movable as one. Belts 32 are also supplemented by supporting rollers placed immediately outside the conveyor to urge belts 32 inwardly on containers 24. The belts 32 can be moved at different speeds as may be needed for container turning, but the average speed should be sufficient to avoid any backlog. The successive axial inspection stations examine each container without the need to space any container from adjacent containers. These inspection stations may include a rim inspection station in which axially-oriented video camera 82 secures an image of a container rim by means of diffuse rim illumination block 84. Absorption analysis adapted to detect residual water in washed containers can also be axially oriented, for example using an infrared source 86 directed axially through the container toward a detector. A capacitance-measuring detector can also be used to detect water. Container base inspection is accomplished using a further video detector 66, operable to capture an image of a container bottom wall through a diffuse panel 64, also illuminated from below by a strobe lamp (not shown).

Figure 8:
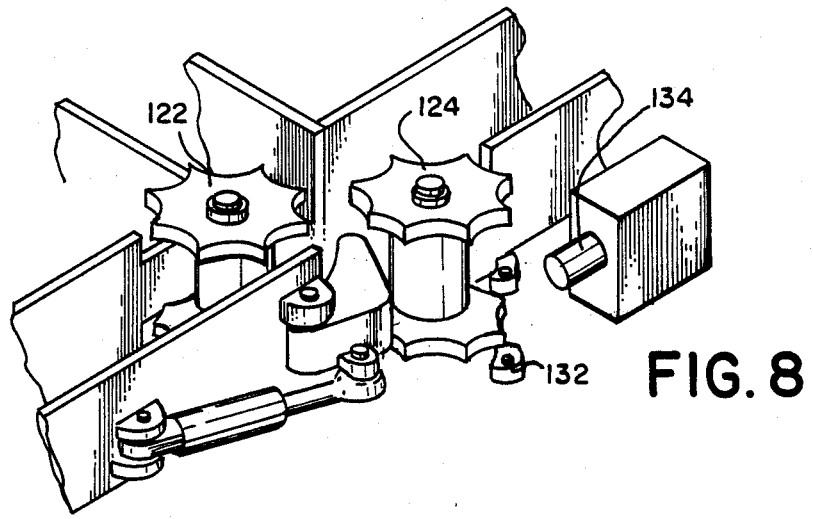
FIG. 8 is a perspective view of a container diverting mechanism according to the invention.
Figure 9:
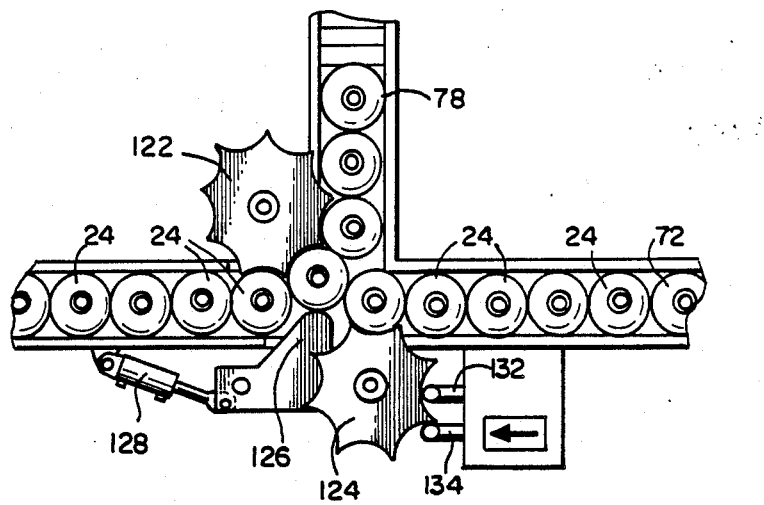
FIGS. 9 and 10 are plan views of the device of FIG. 8, showing respective positions of the bottles and movable protrusion during diverting a bottle and passing a bottle, respectively.
Figure 10:
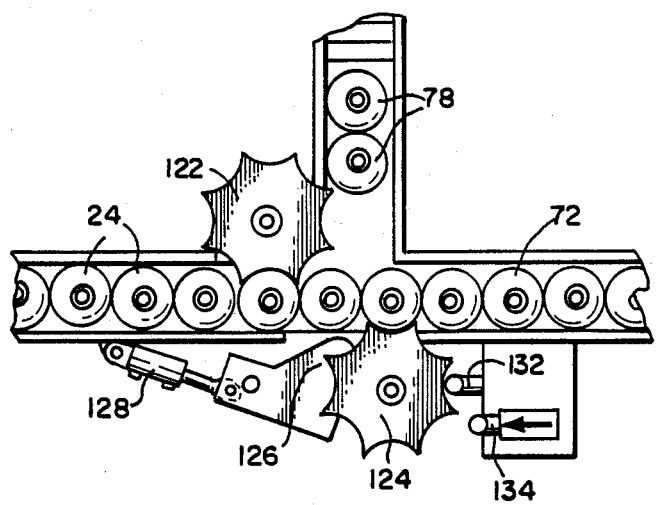

Video signals and other data developed in the video detectors and/or energy absorption detectors can be passed to processor 106 that also associates the rim, absorption and base data with individual containers by counting containers as they advance along the inspection path. Alternatively, upstream devices can apply a dye mark or the like detectable as a rejectable defect by the sidewall inspection device or by a stand-alone dye detector (not shown) associated with a rejection device. Downstream of the means for capturing data, a container sorting mechanism 70 is provided, as shown in FIGS. 8-10. This mechanism is controllable for example by processor 106 and includes an idler star wheel 122, and controllable means by which containers 24 advancing along the conveyor will be allowed to pass straight into path 72, or diverted around idler wheel 122 into diversion path 78. The path 72 and diversion path 78 are defined on respective first and second tangents of the idler star wheel 122. This is accomplished by means of a downstream container stopping device. The stopping device, which is positioned downstream of the idler star wheel 122 by a distance substantially equal to a width of one container, may be an obstruction movable across the conveying path but preferably is a second star wheel 124 that can be stopped from rotating. The container stopping device such as star wheel 124 is controllable together with a movable obstruction 126 that only partly obstructs the path. Bottle stop wheel 124 can be arranged together with a wheel-stopping picker such as a solenoid 134, directed to be movable against the teeth of the star wheel 124. When solenoid 134 is advanced, wheel 124 stops and the bottle at one position ahead of the bottle to be diverted stops. The stoppage of a bottle by the wheel 124 holds the next successive bottle in an area to be engaged by the idler star wheel 122. Otherwise, with solenoid 134 retracted, stop star wheel 124 merely idles, passing all the containers along path 72 as shown in FIG. 10. A photocell pair 132, limit switch or another convenient detector can be used to detect the passage of the teeth of start wheel 124, thereby facilitating both timing of the bottle stop and counting of bottles passing along path 72. The stoppage of the controllable star wheel 124 and the positioning of the obstruction 126 are synchronized to the position of the star wheel 124. At a predetermined time with the passage of each tooth of wheel 124, a time arises during which movable obstruction 126 can be advanced as shown in FIG. 9. Obstruction 126 can be moved in either direction by means of an air cylinder 128 controllable by electrically-activatable air supply valves, or can be wholly electrical such as a solenoid-driven shaft or the like. The conveyor being slightly larger than the bottle, obstruction 126 merely moves a bottle to be diverted slightly past the center line of the conveyor at the same time that star wheel 124 stops the next bottle downstream. Inasmuch as bottles 24 continue at all times to advance at full speed toward idler star wheel 122, the diverted bottleis in position to be squeezed out between the stopped bottle in wheel 124 and the next arriving bottle on idler wheel 122. The effect is to force the diverted bottle around idler star wheel 122, where it is released along the next available tangent, namely path 78. According to such a device, the diversion is accomplished without ever stopping the oncoming containers 24, and with minimal chance of fouling.

Figure 11:
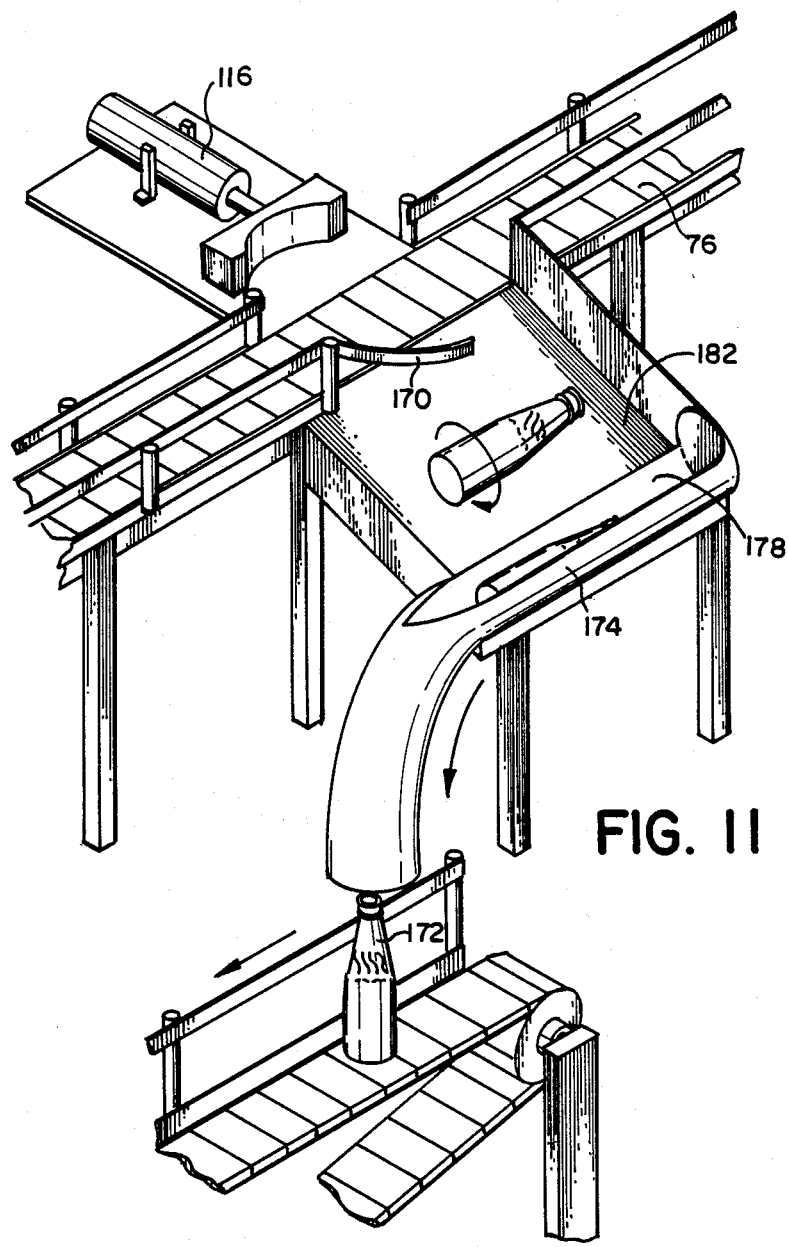
FIG. 11 is a partial perspective view of the rejection device in FIG. 1.

FIG. 11 shows a detailed view of the rejection system downstream of the star wheel rejection mechanism of FIGS. 8–10. Under control of the processor, further selection of diverted containers can be accomplished such that any containers which are rejected for purposes of dirt can be rewashed, etc., rather than simply disposed of, as unusable. Diverted containers move down a path in front of ram cylinder 116, which is operable to controllably force any of the oncoming bottles toward a chute 174, leading to a return conveyor. The return conveyor is preferably at a lower level than the inspection mechanism, to conserve space. The return conveyor can be located wholly or partly underneath the inspection conveyor, as shown in FIG. 1.

Ram 16 forces oncoming containers off their basis by pushing the containers laterally against hook 170, which is disposed laterally off the side of the conveyor and defines a curving path for the upper part of the bottle, causing the bottle to fall to the right as shown in FIG. 11. Containers such as bottles are, of course, top-heavy, and by locating 170 above the center of gravity of the bottle and by pushing the bottle using ram 116 from a point below the center of gravity, the bottle is pushed over on its side, and caused to roll down table 182 into opening178 in chute 174, in the proper orientation. The bottle in the chute simply slides downwardly and is dropped on its base on a return conveyor, where rewash bottles 172, or the like, can be returned for further processing. Other bottles continue along conveyor 76, for further processing or disposal.

The comprehensive system as so disclosed includes a number of features that facilitate continuous operation of the line and allow sophisticated inspection without the need to stop the line, or to engage individual bottles anywhere upstream of the diversion mechanism. A number of variations on the system as disclosed will now become apparent to persons skilled in the art. Reference should be made to the appended claims rather than the foregoing specification as indicating the true scope of the invention.

What is claimed is:

1. An inspection system for analyzing images of continuously moving, closely-spaced bottles, containers and like bodies, comprising:
   triggering means operable to detect the passage of each of the bodies past a predetermined positioned;
   a flash lamp responsive to the triggering means and operable to momentarily illuminate each of the bodies in turn at the predetermined position, and also to illuminate at least one additional body adjacent said each of the bodies in turn;
   a video detector having a solid state planar array and optics to focus and record on the array an image of the body at the predetermined position, a plurality of individual pixels being defined by the image thus focused on the array;
   control means responsive to the triggering means, operative to address the individual pixels in the image recorded in the array;
   memory means defining an image buffer connected to the video detector and operable responsive to the control means to store data representing a single image, said image being collected substantially synchronously with a trigger signal from the triggering means;
   data processing means operable asynchronously with the triggering means, the data processing means being operable to read the data in the image buffer, and to analyze said data asynchronously with the trigger means; and,
   a random access memory connected to the data processing means and operable to store successive ones of the images, each successive image having data representing plural ones of the bodies, the data processing means associating portions of the image of a given body from the plural bodies in successive images, as the given body advances along a conveying path.

2. The inspection system of claim 1, wherein the video detector is a video camera producing an analog level for each a plurality of pixels in the array, and further comprising an analog to digital converter operable to convert the analog level to digital data for storage.

3. The inspection system of claim 1, wherein each recorded image includes a representation of a plurality of containers, and further comprising means for turning the containers while moving in a continuous line.

4. The inspection system of claim 1, further comprising mechanical means downstream of the video detector having controllable means responsive to the processor for diverting bodies in the continuous line to one of at least two paths.

5. An inspection system for transparent and translucent containers continuously moving in a conveying direction along a conveyor, the containers having longitudinal axes, and the conveying direction being perpendicular to said longitudinal axes, the system comprising:
   an axial inspection zone having detector means oriented along the longitudinal axes of the containers, perpendicular to the conveying direction, the detector means being operable to discern features of the containers including at least one of base features, rim features and energy absorption features;
   a side wall inspection zone for examining side walls of the containers, having optical means directed substantially perpendicularly to the axes of the containers, the side wall inspection zone having means for turning the containers, the side wall inspection zone including means recording an image of plural containers in said side wall inspection zone and means associating a portion of successive images of a given container as said container advances in the image; and,
   a mechanical diverter means mounted downstream of the axial inspection zone and side wall inspection zone, operable to divert containers to one of at least two paths, responsive to features detected in the axial zone and the side wall inspection zone.

6. The inspection system of claim 5, wherein the conveyor comprises a plurality of conveyor links supporting the containers from below, and means defining a gap in the conveyor links at the axial inspection zone; and, a support conveyor at the axial inspection zone comprising a pair of opposed belts on opposite sides of the conveyor, the belts being driven to support the containers from the side walls in the axial inspection zone.

7. The inspection system of claim 5, wherein the inspection system includes triggering means operable to detect the passage of each of the bodies past a predetermined position, a flash lamp responsive to the triggering means and operable to momentarily illuminate the body at the predetermined position, a video detector having a solid state planar array, optics to focus on the array an image of the body at the predetermined position, video processing means responsive to the triggering means and operative to access and digitize levels from the array to define pixels in the image recorded in the array, an image buffer connected to the video detector and operable responsive to the video processing means to store data representing a single image, said image being collected synchronously with a trigger signal from the triggering means, and data processing means operative asynchronously with the triggering means, the data processing means operable to read the data in the image buffer, and to analyze said data asynchronously with the triggering means.

8. The inspection system of claim 7, wherein the inspection system is operative to capture and analyze successive images of three successive containers, said image of three containers being captured upon each successive container passing a predetermined location along the conveying path, the data processing means associating sections of successive images reflecting a given container advancing through the inspection zone.

9. The inspection system of claim 5, wherein the means for turning the containers includes a relatively slower means disposed on a first side of the conveyor and a relatively faster moving driven belt disposed on the other side of the conveyor, the conveyors being frictionally engaged between the slower means and the driven belt, the belt being driven at greater velocity than a speed of the conveyor, whereby the bottles are turned in the side wall inspection zone.

10. The inspection system of claim 9, wherein the driven belt is mechanically coupled to the conveyor to move at twice a velocity of the conveyor.

11. The inspection system of claim 5, wherein the means for turning the containers includes a stationary means disposed on a first side of the conveyor and a moving driven belt disposed on the other side of the conveyor, the containers being frictionally engaged between the stationary means and the driven belt, the belt being driven at a different velocity than the conveyor, whereby the bottles are turned in the side wall inspection zone.

12. An improved sorting station for an inspection system of the type having means for discriminating between containers on a conveyor based upon at least one of rim features, side wall features, base features and energy absorption patterns, the containers being successively movable along a conveying path through an inspection device to the sorting station, the improvement comprising:
an idler star wheel operable to engage each successive container advancing along the conveying path, the idler star wheel having a first tangent defining a first path of the containers and a second tangent defining a diverted path;
a container stop on the first path for selectively stopping a container positioned downstream of the idler star wheel by a distance substantially equal to a width of one container, whereby stoppage of a container by the container stop holds a next successive container in an are to be engaged by the idler star wheel, and,
a movable obstruction operable to displace the next successive container following a stopped container past a center line of the first conveying path, whereby the container stop causes the next successive container to be squeezed toward the diverted path between the stopped container and a further successive container behind the next succesive container whereupon said next successive container proceeds to the diverted path.

13. The inspection system of claim 12, wherein the container stop is a controllable star wheel, and further comprising a stop means movably positionable against teeth of the controllable star wheel to operate the container stop.

14. The inspection system of claim 13, further comprising detector means operable to detect passage of teeth of the controllable star wheel, stoppage of the controllable star wheel and positioned of the movable obstruction being synchronized to the position of the controllable star wheel.

15. An inspection system for transparent and translucent containers continuously moving in a conveying direction along a conveyor, the containers having longitudinal axes and the conveying direction being perpendicular to said longitudinal axes, the system comprising:
an axial inspection zone having detector means oriented along the longitudinal axes of the containers, perpendicular to the conveying direction, the detector means being operable to discern features of the containes including at least one of base features, rim features and energy absorption features;
a side wall inspection zone for examining side walls of the containers, having optical means directed substantially perpendicular to the longitudinal axes of the containers, the side wall inspection zone having means for turning the containers;
a mechanical diverter means mounted downstream of the axial inspection zone and side wall inspection zone, operable to divert containers to one of at least two paths, responsive to features detected in the axial inspection zone and the side wall inspection zone, the mechanical diverter including a ram operable to force selected ones of the containers laterally from the conveyor, the ram disposed to push the containers from a point below a center of gravity of the containers, a stationary hook mounted adjacent conveyor, the hook defining an arc for a portion of the containers above said center of gravity, the hook and the ram orienting the containers on their sides, and, a chute positioned to receive the containers, the chute being inclined and having a terminal portion oriented to place the containers on a further conveyor.

16. The inspection system of claim 15, further comprising an inclined table disposed on a side of the conveyor opposite the ram, the hook being located above the table and the chute being disposed at a lateral edge of the table, diverted bottles rolling down the table into the chute.

* * * * *